United States Patent
Burkholz et al.

(10) Patent No.: US 12,246,157 B2
(45) Date of Patent: Mar. 11, 2025

(54) NEEDLELESS ACCESS CONNECTOR FACILITATING INSTRUMENT DELIVERY TO A CATHETER ASSEMBLY

(71) Applicant: Becton, Dickinson and Company, Franklin Lakes, NJ (US)

(72) Inventors: Jonathan Karl Burkholz, Salt Lake City, UT (US); Heena Dani, Middlesex, NJ (US); Megan Scherich, Salt Lake City, UT (US); Derek Jewell, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 871 days.

(21) Appl. No.: 16/738,928

(22) Filed: Jan. 9, 2020

(65) Prior Publication Data
US 2020/0222681 A1 Jul. 16, 2020

Related U.S. Application Data
(60) Provisional application No. 62/792,239, filed on Jan. 14, 2019.

(51) Int. Cl.
*A61M 39/12* (2006.01)
*A61M 25/06* (2006.01)
*A61M 39/24* (2006.01)

(52) U.S. Cl.
CPC ........ *A61M 39/12* (2013.01); *A61M 25/0606* (2013.01); *A61M 39/24* (2013.01); *A61M 2039/2426* (2013.01)

(58) Field of Classification Search
CPC . A61M 39/223; A61M 39/224; A61M 39/105
See application file for complete search history.

(56) References Cited

U.S. PATENT DOCUMENTS 5,242,432 A * 9/1993 DeFrank ............... A61M 39/26
604/83
5,549,566 A * 8/1996 Elias ................... A61M 39/045
604/167.03
(Continued)

FOREIGN PATENT DOCUMENTS

EP 1236482 9/2002
WO 2017/007769 1/2017

OTHER PUBLICATIONS

Hull, Garret J., et al., "Quantitative Assessment of Reflux in Commercially Available Needle-Free IV Connectors.", The Journal of Vascular Access, Wichtig Publishing S.r.l., 2018, vol. 19(I), p. 12-22.

*Primary Examiner* — Courtney B Fredrickson
(74) *Attorney, Agent, or Firm* — Kirton McConkie; Whitney Blair; Kevin Stinger

(57) ABSTRACT

A needleless access connector may include a body, which may include a proximal end configured to couple to an instrument delivery device and a distal end configured to couple to a peripheral intravenous catheter assembly. The needleless access connector may also include an accordion valve disposed within the body between the proximal end and the distal end. The accordion valve may include an accordion portion. In response to compression of the accordion portion and opening of the accordion valve, a straight pathway extending through the proximal end and the distal end may be exposed such that an instrument of the instrument delivery device may move distally from the proximal end to the distal end through the straight pathway without bending.

16 Claims, 15 Drawing Sheets

(56) References Cited

U.S. PATENT DOCUMENTS

| | | | |
|---|---|---|---|
| 5,676,346 A * | 10/1997 | Leinsing | A61M 39/26 604/905 |
| 5,685,866 A | 11/1997 | Lopez | |
| 6,079,432 A * | 6/2000 | Paradis | A61M 39/26 604/167.04 |
| 6,117,114 A * | 9/2000 | Paradis | A61M 39/045 604/533 |
| 8,177,760 B2 * | 5/2012 | Rome | A61M 39/26 604/537 |
| 8,366,685 B2 | 2/2013 | Devgon | |
| 9,186,100 B2 | 11/2015 | Devgon | |
| 9,744,344 B1 | 8/2017 | Devgon et al. | |
| 2001/0021829 A1 * | 9/2001 | Hiejima | A61M 5/16877 604/247 |
| 2002/0147431 A1 * | 10/2002 | Lopez | A61M 39/045 604/537 |
| 2003/0098430 A1 * | 5/2003 | Leinsing | A61M 39/26 604/905 |
| 2003/0209681 A1 * | 11/2003 | Leinsing | A61M 39/26 604/905 |
| 2004/0127854 A1 | 7/2004 | Leinsing et al. | |
| 2006/0173420 A1 * | 8/2006 | Fangrow | A61M 39/24 604/247 |
| 2014/0188002 A1 | 7/2014 | Close et al. | |
| 2015/0374910 A1 * | 12/2015 | Mansour | A61M 1/782 604/500 |
| 2016/0129235 A1 | 5/2016 | Ryan | |
| 2016/0250413 A1 * | 9/2016 | Good | A61M 39/24 137/625.4 |
| 2016/0331893 A1 * | 11/2016 | Yeh | A61M 5/1411 |
| 2017/0216564 A1 | 8/2017 | Devgon et al. | |
| 2017/0360345 A1 | 12/2017 | Devgon | |
| 2018/0256885 A1 * | 9/2018 | Shevgoor | A61M 25/0606 |

\* cited by examiner

NEEDLELESS ACCESS CONNECTOR FACILITATING INSTRUMENT DELIVERY TO A CATHETER ASSEMBLY

RELATED APPLICATIONS

This application claims the benefit of U.S. Provisional Patent Application No. 62/792,239, filed Jan. 14, 2019, and entitled NEEDLELESS ACCESS CONNECTOR FACILITATING INSTRUMENT DELIVERY TO A CATHETER ASSEMBLY, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter may be more susceptible to narrowing, collapse, kinking, blockage by debris (e.g., fibrin or platelet clots), and adhering of a tip of the catheter to the vasculature. Due to this, catheters may often be used for acquiring a blood sample at a time of catheter placement but are much less frequently used for acquiring a blood sample during the catheter dwell period. Therefore, when a blood sample is required, an additional needle stick is needed to provide vein access for blood collection, which may be painful for the patient and result in higher material costs. Accordingly, there is a need for catheter systems and methods that facilitate placement of blood sample instruments, such as, for example, catheters and probe instruments, in the vasculature of the patient without additional needle sticks.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to needleless access connectors ("NACs"), and related systems and methods. In some embodiments, a NAC may include a body, which may include a proximal end configured to couple to an instrument delivery device and a distal end configured to couple to a peripheral intravenous catheter assembly. In some embodiments, the NAC may also include an accordion valve disposed within the body between the proximal end and the distal end.

In some embodiments, the accordion valve may include an accordion portion. In some embodiments, in response to compression of the accordion portion and opening of the accordion valve, a straight pathway extending through the proximal end and the distal end may be exposed such that an instrument of the instrument delivery device may move distally from the proximal end to the distal end through the straight pathway without bending.

In some embodiments, the NAC may include a post configured to extend through the accordion valve when the accordion valve is open. In some embodiments, a proximal end of the post may be flexible. In some embodiments, the accordion valve may include a rigid portion, which may be disposed proximal to the accordion portion. In some embodiments, the rigid portion may be disposed on an inner surface of the accordion valve. In some embodiments, the rigid portion may contact the post. In some embodiments, a proximal end of the accordion valve may include the rigid portion.

In some embodiments, the NAC may include a male luer fitting configured to slide between a proximal position and a distal position. In some embodiments, in response to the male luer fitting sliding from the proximal position to the distal position, the male luer fitting may contact a proximal end of the accordion valve and move the accordion valve distally. In some embodiments, the accordion valve may include a slit. In some embodiments, the slit may open in response to contact from the male luer fitting and prior to the accordion valve contacting the post. In some embodiments, in response to the male luer fitting sliding from the proximal position to the distal position, the accordion valve may open on the post.

In some embodiments, the NAC may include an anti-reflux valve, which may be disposed within the body between the proximal end and the distal end. In some embodiments, the NAC may include another anti-reflux valve disposed within the body between the proximal end and the distal end. In some embodiments, the body may be monolithically formed as a single unit. In some embodiments, the body may include a first piece that includes the anti-reflux valve and a second piece that comprises the accordion valve. In some embodiments, a luer fitting of the first piece may be coupled to a corresponding luer fitting of the second piece. In some embodiments, the second piece may include a side port and an extension tube extending from the side port.

In some embodiments, the distal end of the NAC may be coupled to the peripheral intravenous catheter assembly. In some embodiments, the NAC may include a side port. In some embodiments, wherein the side port may include a positive or neutral displacement ("PND") valve. In some embodiments, the PND valve may be compressible such that fluid flows around an outer surface of the PND valve to pass the PND valve.

In some embodiments, the side port and the PND valve may be disposed at 90 degrees with respect to a longitudinal axis of the NAC. In some embodiments, the side port and the PND valve may be disposed at less than 90 degrees with respect to the longitudinal axis of the NAC, which may facilitate insertion of the instrument therethrough in a distal direction. In some embodiments, the side port and the PND valve may be disposed at greater than 90 degrees with respect to the longitudinal axis of the NAC, which may facilitate flushing of the side port the and NAC.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
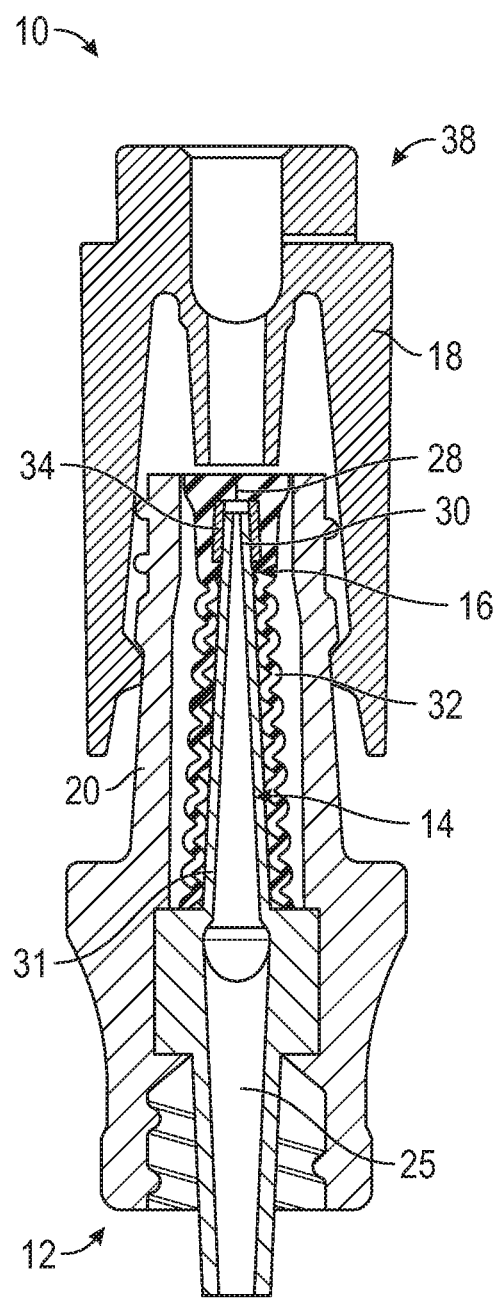
FIG. 1A is a cross-sectional view of an example NAC, illustrating an example male luer fitting of the NAC in a proximal position, according to some embodiments.
Figure 1B:
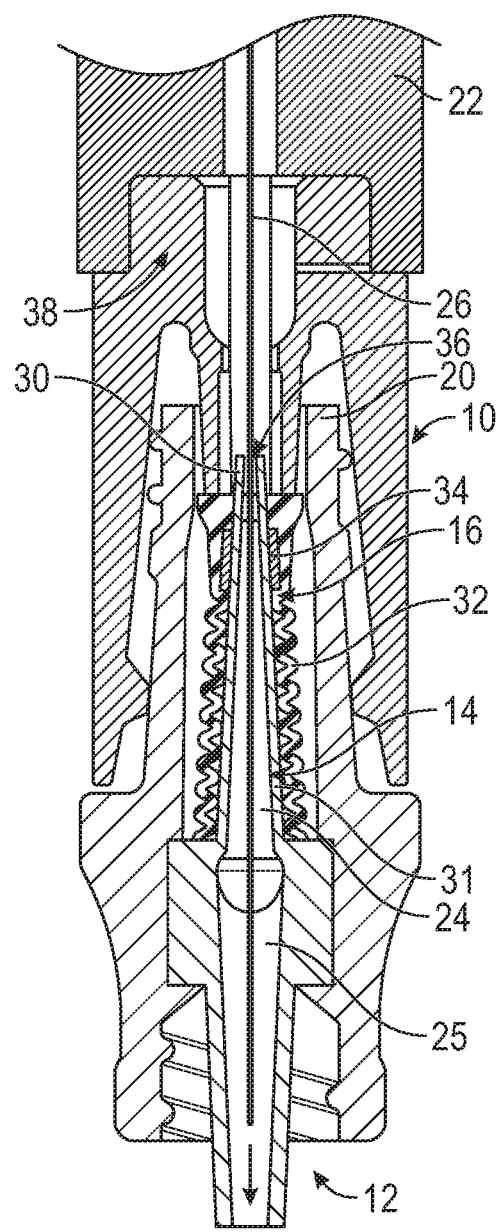
FIG. 1B is a cross-sectional view of the NAC, illustrating an example instrument delivery device coupled to a proximal end of the NAC and the male luer fitting in a distal position, according to some embodiments.
Figure 1C:
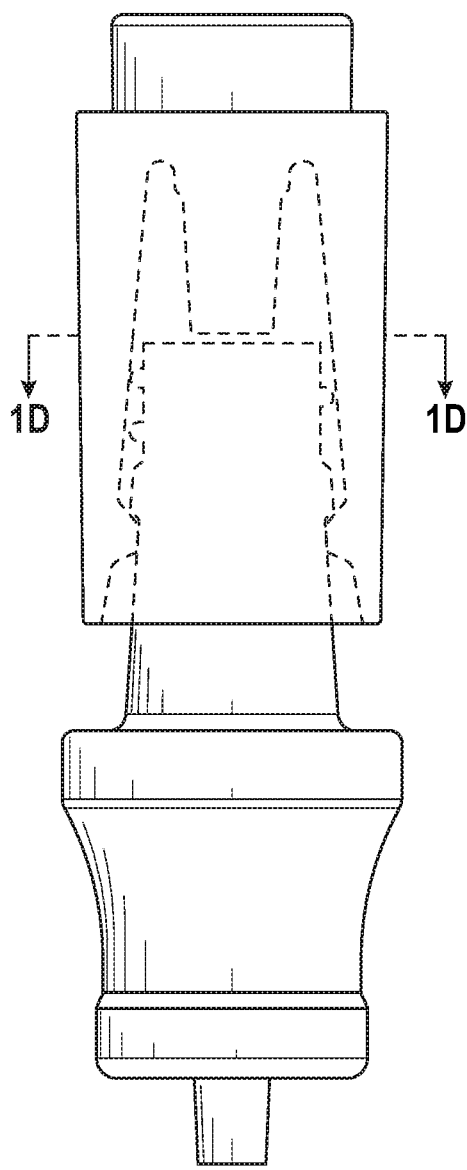
FIG. 1C is an upper perspective view of the NAC, illustrating the male luer fitting in the proximal position, according to some embodiments.
Figure 1D:
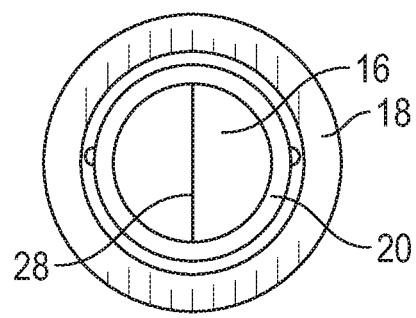
FIG. 1D is a cross-sectional view of the NAC along the line 1D-1D of FIG. 1C, according to some embodiments.

The present disclosure relates generally to needleless access connectors ("NACs"), and related systems and methods. Referring now to FIGS. 1A-1D, an example NAC 10 is illustrated, according to some embodiments. In some embodiments, the NAC 10 may provide access to a vascular system of a patient when a distal end 12 of the NAC 10 is coupled to a vascular access device. In some embodiments, the vascular access device may include a catheter assembly, such as, for example, a peripheral intravenous catheter ("PIVC") assembly. In some embodiments, the vascular access device and the NAC 10, coupled together, may be used for blood collection, fluid delivery, patient or device monitoring, or other clinical needs.

In some embodiments, the NAC 10 may include a post 14 within the NAC 10 and a accordion valve 16 extending over the post 14. In some embodiments, the NAC 10 may include a male luer fitting 18, which may slide between a proximal position, illustrated, for example, in FIG. 1A, and a distal position, illustrated, for example, in FIG. 1B. In some embodiments, when the male luer fitting 18 is in the distal position, the male luer fitting 18 may be disposed within a female luer fitting 20 of the NAC 10.

In some embodiments, an instrument delivery device 22, or another medical device, may be coupled to the male luer fitting 18. In some embodiments, the male luer fitting 18 may be advanced from the proximal position to the distal position following or in response to coupling of the instrument delivery device 22 to the proximal end of the male luer fitting 18. In some embodiments, in response to movement of the male luer fitting 18 from the proximal position to the distal position, the male luer fitting 18 may contact the accordion valve 16, and the accordion valve 16 may move distally. Additionally, in some embodiments, the post 14 may penetrate the accordion valve 16. In some embodiments, a portion of the accordion valve 16 may remain between the male luer fitting 18 and the post 14 when the male luer fitting 18 is disposed in the distal position.

In some embodiments, when the accordion valve 16 is opened, the NAC 10 may provide a straight and direct pathway 24 through a lumen 25 of the NAC 10, which may facilitate advancement of an instrument 26 through the NAC 10 and/or the vascular access device into vasculature of the patient. In some embodiments, the pathway 24 may be a fluid pathway. In some embodiments, the lumen 25 may extend through the NAC 10. In some embodiments, the instrument 26 may include tubing for fluid infusion or blood draw, a guidewire, a probe with a sensor, or a light tube for disinfection.

In some embodiments, the post 14 having the opening 36 extending therethrough may support the accordion valve 16 and may facilitate guidance of the instrument 26 distally through the NAC 10. In some embodiments, the instrument delivery device 22 may include an advancement tab or another mechanism to advance the instrument 26 distally into the NAC 10 and/or into the vascular access device. In some embodiments, a portion of the instrument 26 may be secured within the instrument delivery device 22. A non-limiting example of an instrument delivery device is described in U.S. Patent Application No. 62/696,229, filed Jul. 10, 2018, entitled "DELIVERY DEVICE FOR A VASCULAR ACCESS INSTRUMENT," which is hereby incorporated by reference in its entirety.

In some embodiments, the accordion valve 16 may open on the post 14 in response to movement of the male luer fitting 18 from the proximal position to the distal position. In some embodiments, the accordion valve 16 may include a slit 28, which may facilitate opening of the accordion valve 16 on the post 14 or just prior to contact with the post 14. In some embodiments, the slit 28 may prevent coring of the accordion valve 16 by the post 14. In some embodiments, the post 14 may be shortened, and the accordion valve 16 may be molded with the slit 28 open to allow pre-opening of the accordion valve 16 prior to the accordion valve 16 contacting the post 14 and reduce a likelihood of the post 14 coring the accordion valve 16. In some embodiments, the accordion valve 16 may not include the slit 28, and the post 14 may pierce the accordion valve 16 to open the accordion valve 16. In some embodiments, a proximal end 30 of the post 14 may be blunt and/or tapered. In some embodiments, an inner diameter of the proximal end 30 of the post 14 may include one or more lead-in features to funnel or guide the instrument 26 into the post 14.

In some embodiments, the accordion valve 16 may include a pleated or accordion portion 32, which may be configured to collapse distally in response to movement of the male luer fitting 18 from the proximal position to the distal position. In some embodiments, at least a portion of the accordion valve 16 may include a flexible material. In some embodiments, at least a portion of the accordion valve 16 may include silicone or another suitable material.

In some embodiments, the accordion valve 16 may include a rigid portion 34, which may contact the post 14 in response to movement of the male luer fitting 18 from the proximal position to the distal position. In some embodiments, the rigid portion 34 may maintain integrity of the accordion valve 16 and protect against coring of the accordion valve 16 on the post 14. In some embodiments, the rigid portion 34 may be disposed on an inner portion of the accordion valve 16. In some embodiments, the rigid portion 34 may contact the post 14 prior to and/or in response to insertion of the male luer fitting 18 into the female luer fitting 20. In some embodiments, the rigid portion 34 may line the accordion valve 16. In some embodiments, the rigid portion 34 may not conform into an accordion shape in response to movement of the male luer fitting 18 from the proximal position to the distal position. In some embodiments, a portion of the accordion valve 16 distal to the rigid portion 34 may include an accordion shape in response to movement of the male luer fitting 18 from the proximal position to the distal position.

In some embodiments, the post 14 may be annular having an opening 36 extending therethrough. In some embodiments, a diameter of the opening 36 extending through the post 14 may be greater than an outer diameter of the instrument 26 such that the instrument 26 may easily pass through the post 14 in a distal direction to the vascular access device. In some embodiments, the opening 36 may form at least a portion of the pathway 24. In some embodiments, an outer diameter of the proximal end 30 of the post 14 may be less than an inner diameter of a portion of the male luer fitting 18 disposed within the NAC 10 such that the proximal end 30 of the post 14 may be disposed within the portion of the male luer fitting 18 disposed within NAC 10.

In some embodiments, the distal end 12 of the NAC 10 may include another luer fitting, such as, for example, a slip or thread male or female luer fitting. In some embodiments, the instrument delivery device 22 may be coupled to a proximal end 38 of the NAC 10 in any number of ways. For example, the instrument delivery device 22 may be coupled to the proximal end 38 of the NAC 10 via a slip or thread luer fitting or a non-luer fitting.

Figure 2A:
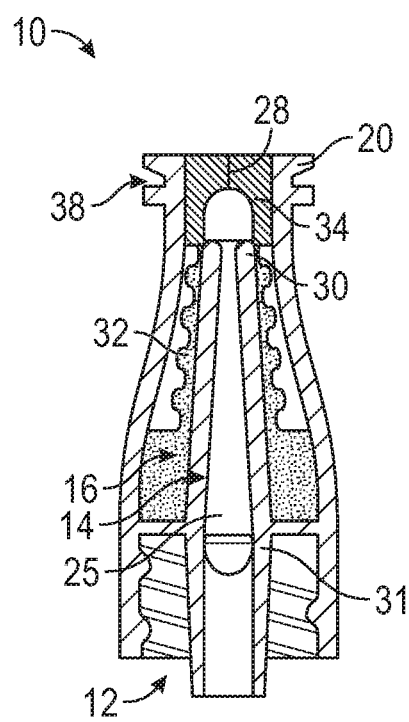
FIG. 2A is a cross-sectional view of the NAC, illustrating an example rigid portion of an example accordion valve, according to some embodiments.
Figure 2B:
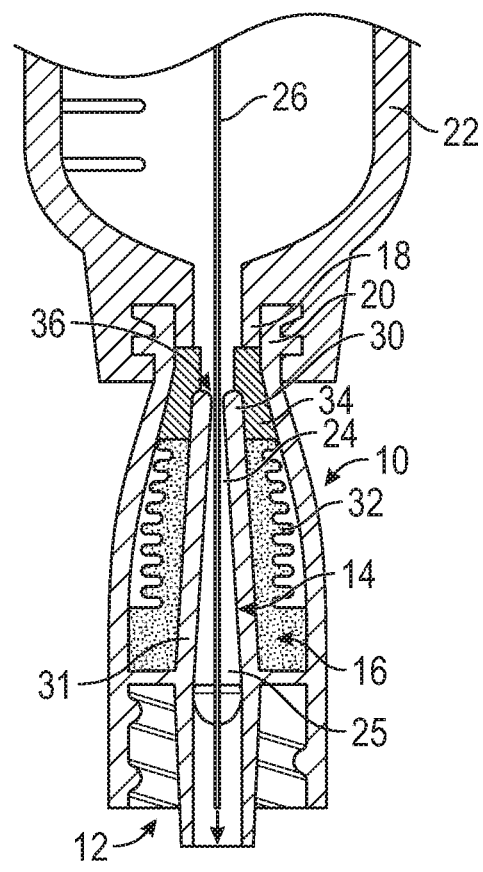
FIG. 2B is a cross-sectional view of the NAC, illustrating another example male luer fitting inserted into the NAC, according to some embodiments.

Referring now to FIGS. 2A-2B, in some embodiments, the male luer fitting 18 that activates the accordion valve 16 and opens the pathway 24 may be disposed on a separate device from the NAC 10, such as on a particular instrument delivery device 22. In some embodiments, the proximal end 38 of the NAC 10 may include the female luer fitting 20. In some embodiments, in response to coupling of the instrument delivery device 22 to the NAC 10, the male luer fitting 18 may contact the accordion valve 16, and the accordion valve 16 may move distally. Additionally, in some embodiments, the post 14 may penetrate the accordion valve 16. In some embodiments, the rigid portion 34 of the accordion valve 16 may remain between the male luer fitting 18 and the post 14 when the instrument delivery device 22 is coupled to the NAC 10.

In some embodiments, the accordion valve 16 may open on the post 14 in response to coupling of the instrument delivery device 22 to the NAC 10. In some embodiments, the accordion valve 16 may include the slit 28, which may facilitate opening of the accordion valve 16 on the post 14 or just prior to contact with the post 14. In some embodiments, the accordion valve 16 may open in response to being pushed distally by the male luer fitting 18. In some embodiments, the accordion valve 16 may include the pleated or accordion portion 32, which may be configured to compress distally in response to coupling of the instrument delivery device 22 to the NAC 10. In some embodiments, the rigid portion 34 may include a portion of a proximal end of the accordion valve 16. In some embodiments, the rigid portion 34 may include an entirety of a proximal end of the accordion valve 16. In some embodiments, the rigid portion 34 may contact the post 14 and/or the male luer fitting 18.

Figure 3A:
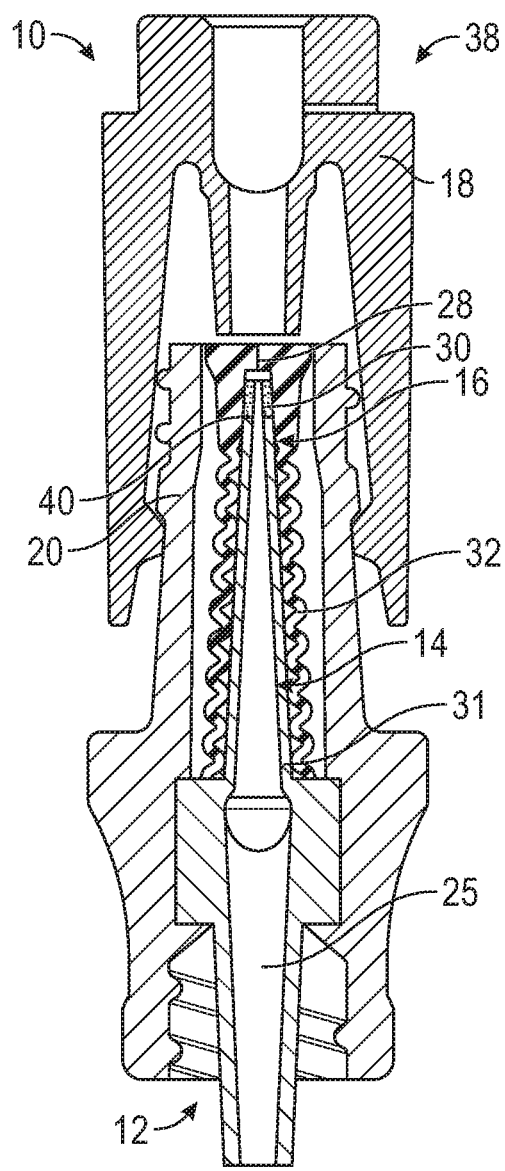
FIG. 3A is a cross-sectional view of the NAC, illustrating an example post and the male luer fitting in the proximal position, according to some embodiments.
Figure 3B:
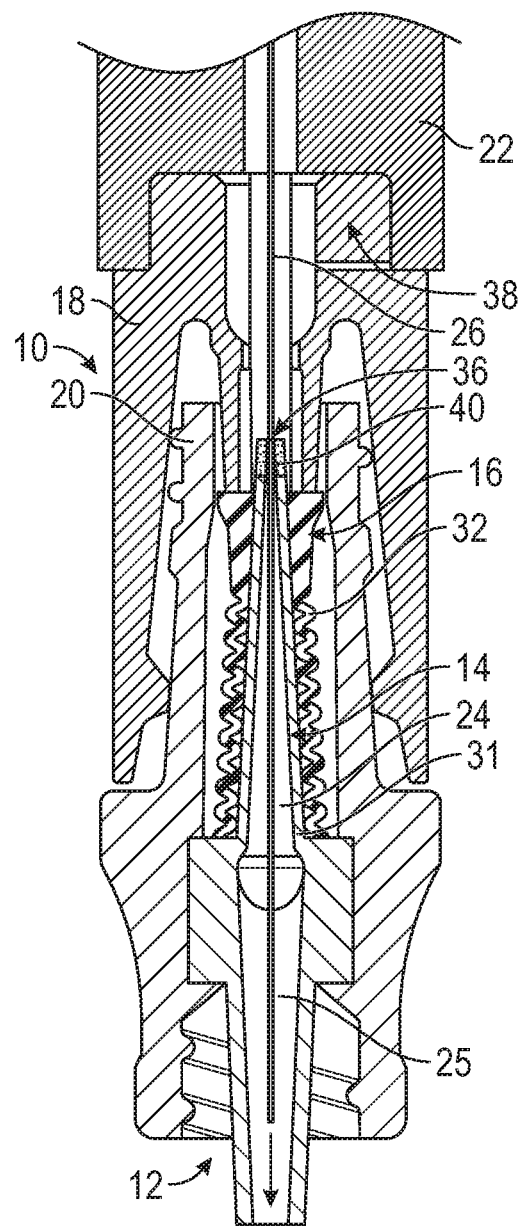
FIG. 3B is a cross-sectional view of the NAC, illustrating the male luer fitting in the distal position, according to some embodiments.
Figure 4A:
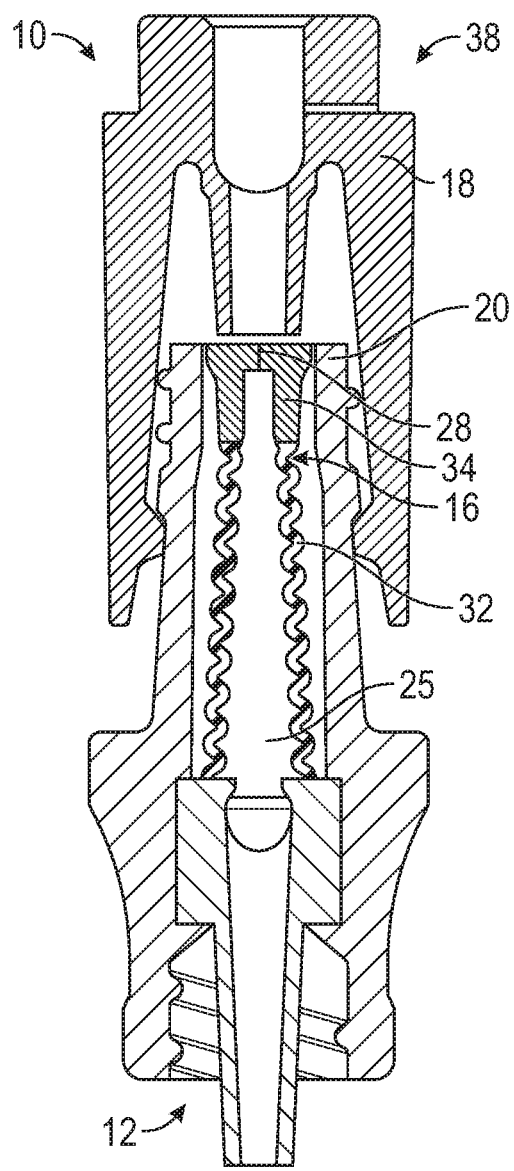
FIG. 4A is a cross-sectional view of the NAC without the post, according to some embodiments.
Figure 4B:
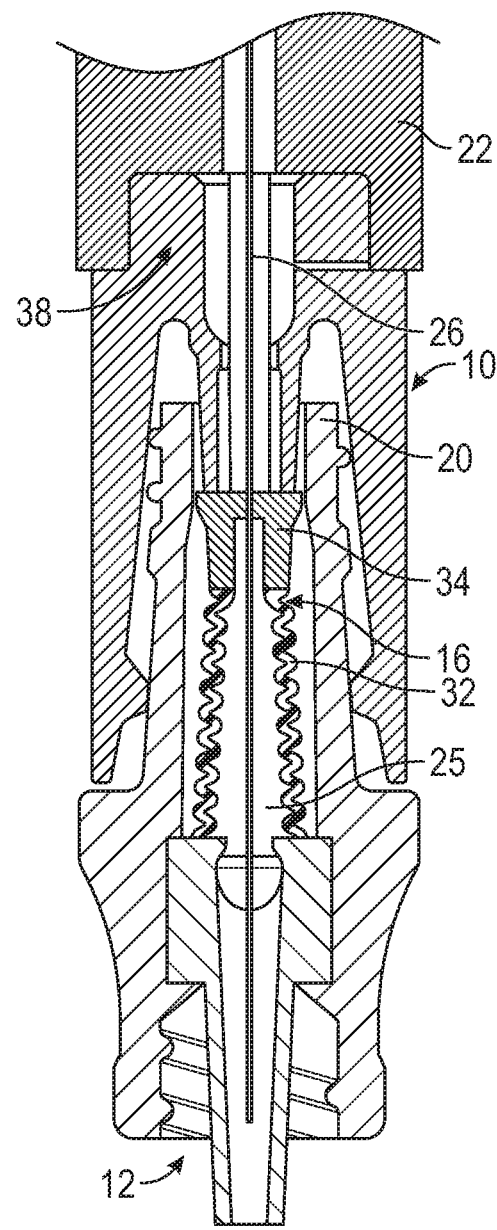
FIG. 4B is a cross-sectional view of the NAC without the post, illustrating the male luer fitting in the distal position, according to some embodiments.

Referring now to FIGS. 3A-3B, in some embodiments, the proximal end 30 of the post 14 may include a cap portion 40, which may include a softer and more flexible material than a distal end 31 of the post 14. In some embodiments, the cap portion 40 may interface with the accordion valve 16 and may prevent coring of the accordion valve 16 after multiple uses. In some embodiments, the post 14 may be replaced with opposing pins, which may each include a cap portion 40 at its proximal end. Referring now to FIGS. 4A-4B, in some embodiments, the NAC 10 may not include the post 14.

Figure 5A:
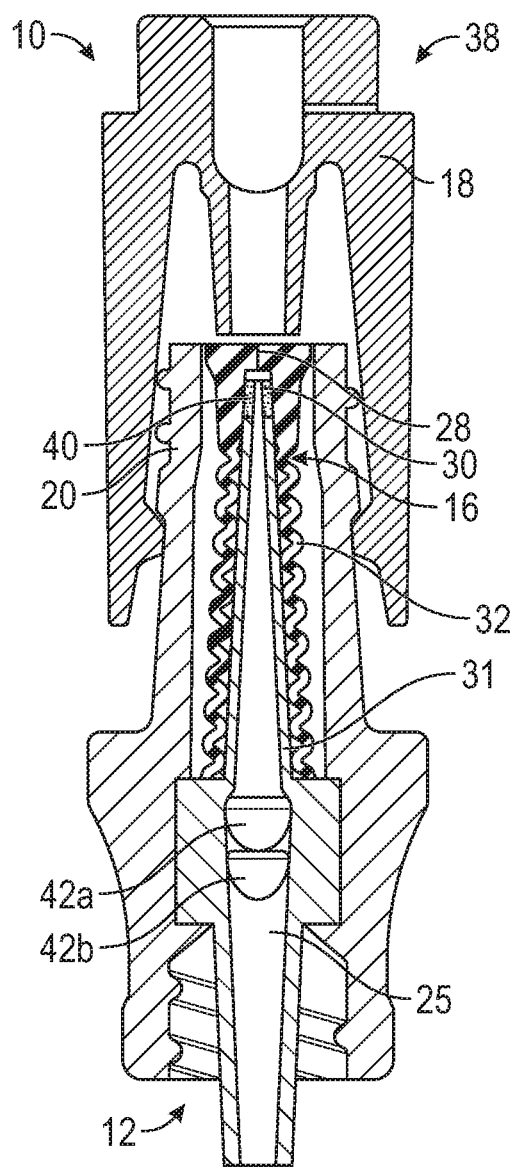
FIG. 5A is a cross-sectional view of the NAC, illustrating example anti-reflux valves, according to some embodiments.
Figure 5B:
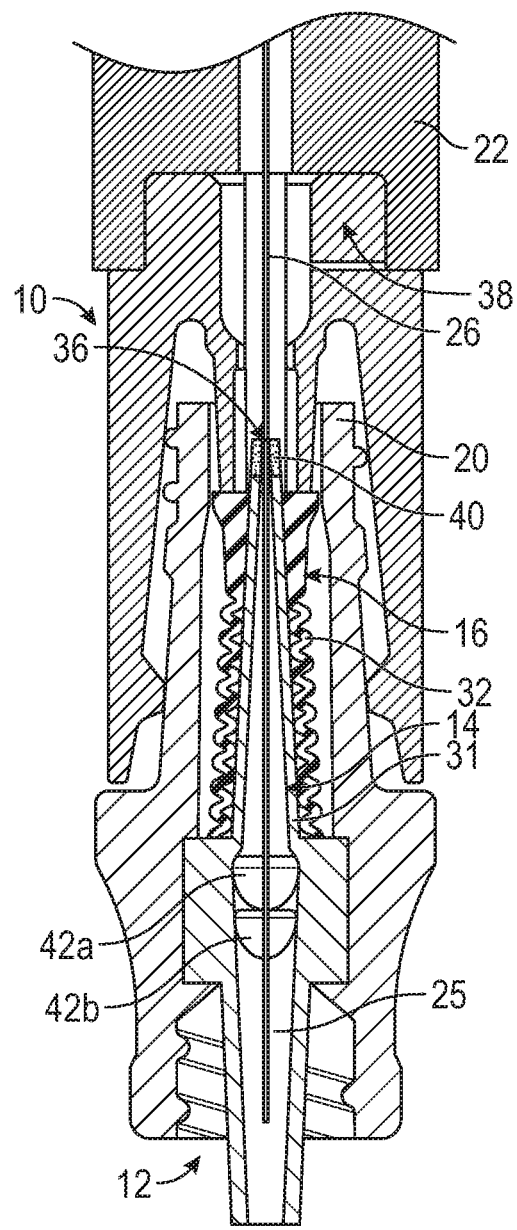
FIG. 5B is a cross-sectional view of the NAC, illustrating the anti-reflux valves and male luer fitting in the distal position, according to some embodiments.

Referring now to FIGS. 5A-5B, in some embodiments, the NAC 10 may include one or more anti-reflux valves 42 positioned within the lumen 25 of the NAC 10. In some embodiments, the NAC 10 may include a first anti-reflux valve 42a and/or a second anti-reflux valve 42b (which may be referred to collectively as "anti-reflux valves 42"), which may be disposed distal to the first anti-reflux valve 42a. In some embodiments, the first anti-reflux valve 42a and/or the second anti-reflux valve 42b may be bi-directional, and thus, may open for fluid administration or aspiration. In some embodiments, the first anti-reflux valve 42a and/or the second anti-reflux valve 42b may be one-way valves.

In some embodiments, the anti-reflux valves 42 may be bell-shaped or tapered, which may facilitate threading of the instrument through the anti-reflux valves 42. In some embodiments, the anti-reflux valves 42 may include a slit extending therethrough. In some embodiments, the slit may be opened by the instrument 26. In some embodiments, the anti-reflux valves 42 may seal the lumen 25 when the instrument 26 is removed from the anti-reflux valves 42 to prevent reflux upon uncoupling of the NAC 10 from the vascular access device. In some embodiments, the anti-reflux valves 42 may protect against microbial ingress. In some embodiments, the anti-reflux valves 42 may be disposed distal to the post 14 and/or the accordion valve 16.

Figure 6:
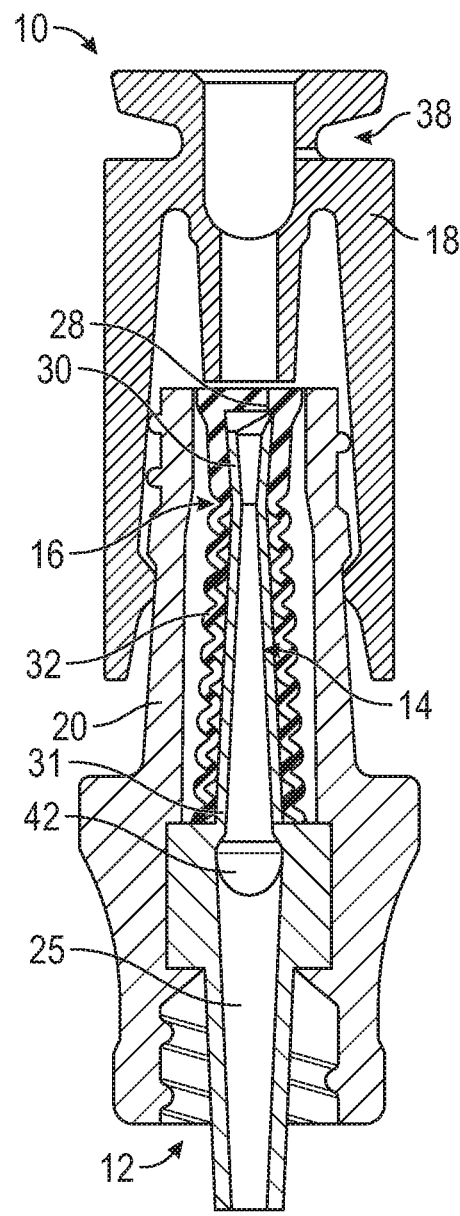
FIG. 6 is a cross-sectional view of the NAC, illustrating the accordion valve having an off-center slit, according to some embodiments.

Referring now to FIG. 6, in some embodiments, the slit 28 may be off-center or not aligned with a longitudinal axis 44 of the NAC 10, which may extend through the opening 36. In some embodiments, a portion of the proximal end 30 of the post 14 that first contacts the accordion valve 16 adjacent the slit 28 in response to movement of the male luer fitting 18 from the proximal position to the distal position and/or coupling of the instrument delivery device 22 to the NAC 10 may also be off-center or asymmetrical. In these and other embodiments, the pathway 24 may provide a straight pathway, such that the instrument 26 moving distally through the NAC 10 may extend through the NAC 10 and/or along the longitudinal axis 44 without bending or changing direction. In some embodiments, a portion of the proximal end 30 of the post 14 that first contacts the accordion valve 16 and pierces the accordion valve 16 in response to movement of the male luer fitting 18 from the proximal position to the distal position and/or coupling of the instrument delivery device 22 to the NAC 10 may be off-center.

Figure 7:
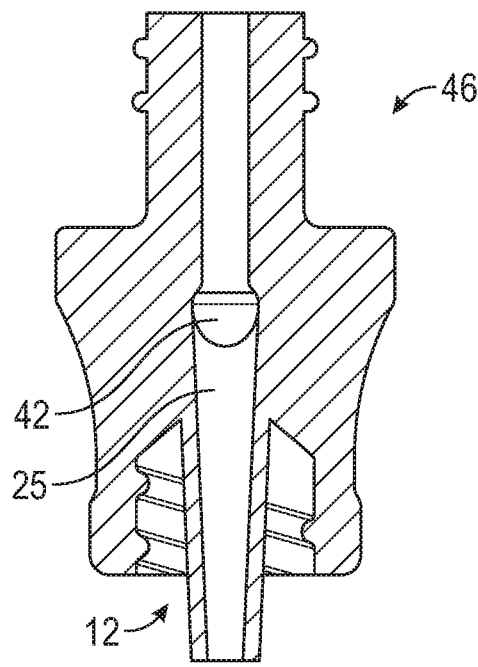
FIG. 7 is a cross-sectional view of an example distal piece, according to some embodiments.

Referring now to FIG. 7, in some embodiments, a portion 46 of the NAC 10 that includes the one or more anti-reflux valves 42 may be a separate unit that is coupled to another portion of the NAC 10 that includes the accordion valve 16 and/or the post 14. In some embodiments, the portion of the NAC 10 that includes the anti-reflux valves 42 may be coupled to the other portion of the NAC 10 that includes the accordion valve 16 and/or the post via a luer fitting, such as, for example, slip or thread male or female fitting. In other embodiments, the portion of the NAC 10 that includes the anti-reflux valves 42 and the other portion of the NAC 10 that includes the accordion valve 16 and/or the post may be monolithically formed as a single unit.

Figure 8A:
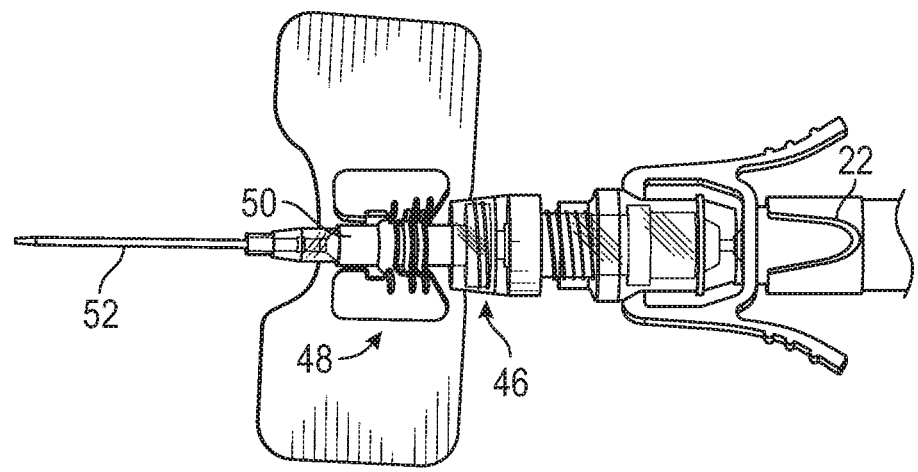
FIG. 8A is an upper perspective view of the NAC coupled to an example catheter assembly, according to some embodiments.
Figure 8B:
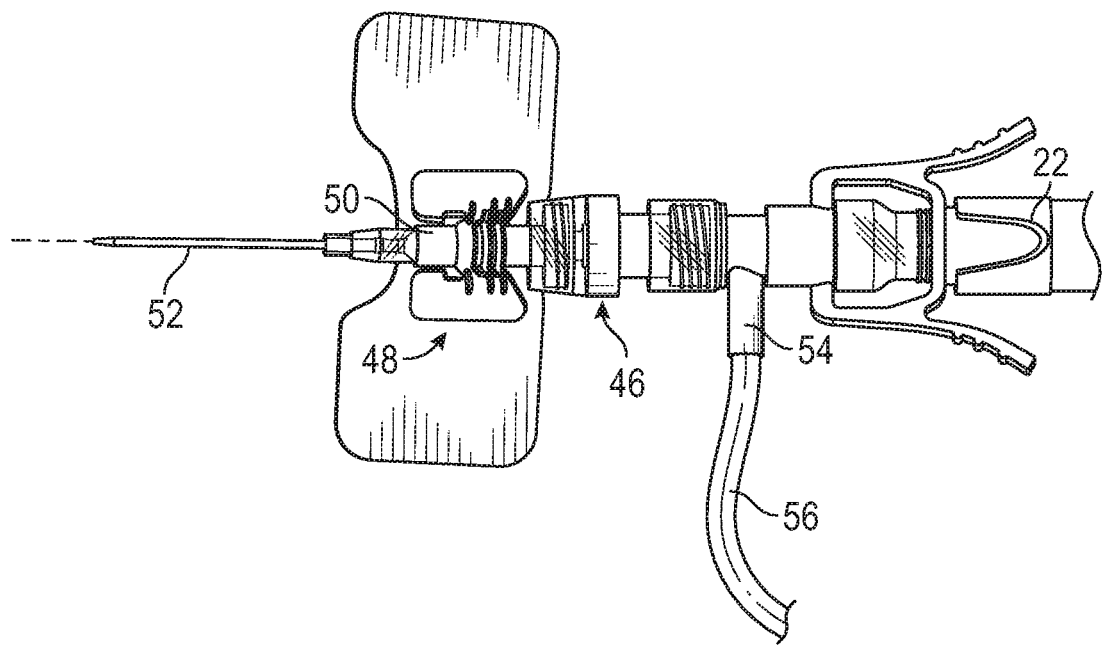
FIG. 8B is an upper perspective view of the NAC coupled to the catheter assembly, illustrating an example extension tube, according to some embodiments.

Referring now to FIGS. 8A-8B, an example vascular access device is illustrated, according to some embodiments. As mentioned, in some embodiments, the vascular access device may include a catheter assembly 48, such as, for example, a PIVC assembly. In some embodiments, the catheter assembly 48 and the NAC 10, coupled together, may be used for blood collection, fluid delivery, patient or device monitoring, or other clinical needs.

In some embodiments, the catheter assembly 48 may include a catheter adapter 50, and a catheter 52 extending distally from the catheter adapter 50. The catheter assembly 48 may include any suitable catheter assembly. In some embodiments, the catheter adapter 50 may include a side port with an integrated extension tube. In some embodiments, as illustrated in FIGS. 8A-8B, for example, the catheter adapter 50 may not include a side port and integrated extension tube.

In some embodiments, the catheter 52 may include a PIVC. In some embodiments, the catheter assembly 48 may be removably coupled to a needle assembly (not illustrated), which may include a needle hub and an introducer needle. In some embodiments, in response to the introducer needle being inserted into a vein of the patient, flashback of blood may flow through a sharp distal tip of the introducer needle and may be visible to a clinician between the introducer needle and the catheter 52 and/or at another location within the catheter assembly 48.

In some embodiments, in response to confirmation via the blood flashback that the catheter 52 is positioned within vasculature of the patient, the needle assembly may be removed from the catheter assembly 48. In some embodiments, when the needle assembly is coupled to the catheter assembly 48, the introducer needle may extend through a septum disposed within a lumen of the catheter adapter 50. In some embodiments, the NAC 10 may be coupled to the proximal end of the catheter adapter 50 after the needle assembly is removed from the catheter adapter 50. In some embodiments, the NAC 10 may include a side port 54 and an extension tube 56 integrated with the side port 54. In some embodiments, the portion 46 of the NAC 10 that includes the anti-reflux valves 42 and the other portion of the NAC 10 that includes the accordion valve 16 and/or the post 14 may be coupled together.

Figure 9A:
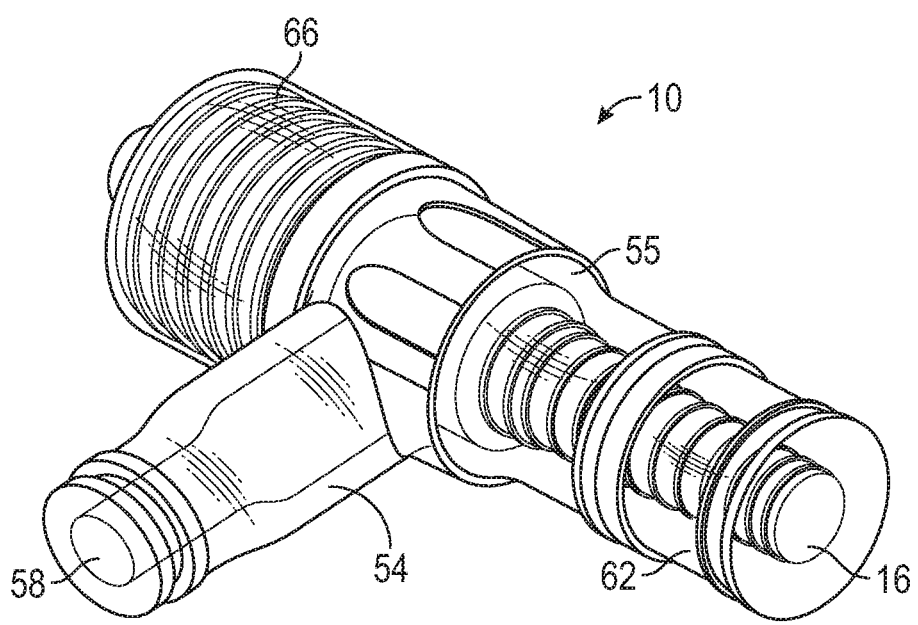
FIG. 9A is an upper perspective view of the NAC, illustrating a side port, according to some embodiments.

Referring now to FIG. 9A, in some embodiments, the NAC 10 may include the side port 54 and/or a housing or body 55 of the NAC 10 may be monolithically formed as a single unit. In some embodiments, the side port 54 may extend perpendicular to the longitudinal axis 44 of the NAC 10 such that the NAC 10 includes a T-shape. In some embodiments, the side port 54 may be angled less than 90° with respect to the longitudinal axis 44 such that the NAC 10 includes a Y-shape (as illustrated, for example, in FIGS. 9F-9H).

Figure 9B:
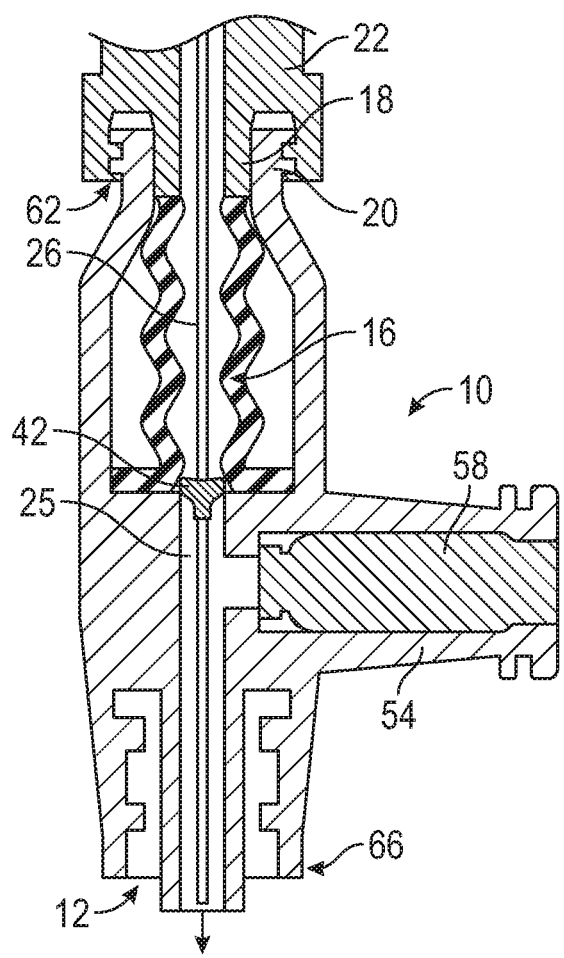
FIG. 9B is a cross-sectional view of the NAC, illustrating the side port and a particular anti-reflux valve in a first location, according to some embodiments.
Figure 9C:
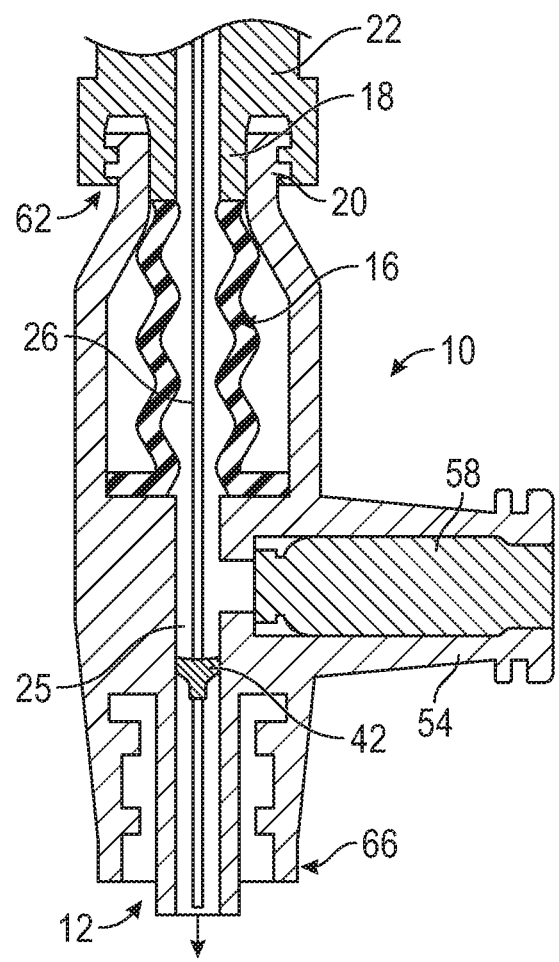
FIG. 9C is a cross-sectional view of the NAC, illustrating the side port and a particular anti-reflux valve in a second location, according to some embodiments.
Figure 9D:
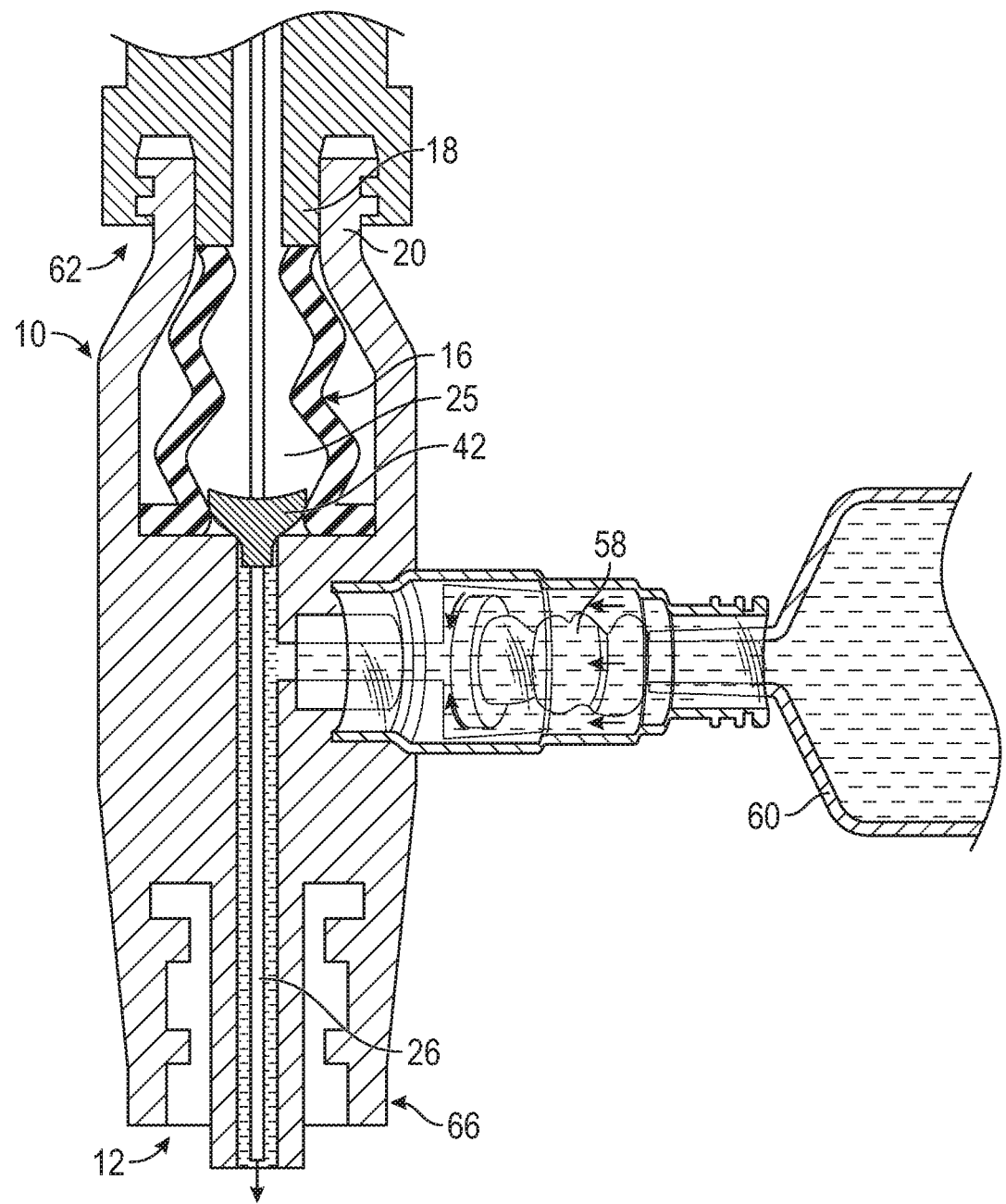
FIG. 9D is a cross-sectional view of the NAC, illustrating the side port and an example medical device coupled to the side port, according to some embodiments.

Referring now to FIGS. 9B-9D, in some embodiments, the side port 54 may include a positive or neutral displacement ("PND") valve 58, which may provide neutral or positive fluid displacement upon uncoupling of a medical device 60 from the side port 54. The term "positive displacement" refers to fluid being pushed out of the NAC 10. The fluid that is pushed out of the NAC 10 may be pushed into the catheter 52 and/or into the patient. The term "negative displacement" refers to fluid being pulled from the patient into the catheter 52 and possibly then being pulled into the NAC 10.

In some embodiments, the NAC 10 may provide neutral or positive fluid displacement upon disconnection with a medical device at the proximal end 38 and/or a medical device at the side port 54, such as the medical device 60, for example. In some embodiments, the accordion valve 16 and/or the PND valve 58 may contribute to the neutral or positive fluid displacement. In some embodiments, when a first medical device is uncoupled from the proximal end 38 of the NAC 10 and/or a second medical device is uncoupled from the side port 54, fluid may be pushed out of the NAC 10 to overcome the intraluminal blood reflux. In some embodiments, the NAC 10 providing neutral fluid displacement may prevent fluid from moving into the catheter adapter 50 from the NAC 10 upon coupling or uncoupling of a particular medical device and the NAC 10.

In some embodiments, the PND valve 58 may be compressible and/or solid. In some embodiments, the PND valve 58 may not include a fluid pathway through the PND valve 58. In some embodiments, fluid may flow around the PND valve 58 in response to coupling of the medical device 60 to the side port 54, as illustrated, for example, in FIG. 9C. In some embodiments, the PND valve 58 may be disposed within the proximal port 62, and the accordion valve 16 and/or the post 14 may be disposed within the side port 54.

In some embodiments, the one or more anti-reflux valves 42 may be disposed in various locations. In some embodiments, a particular anti-reflux valve 42 may be disposed proximal to a junction of a side port fluid pathway with the pathway 24, as illustrated, for example, in FIG. 9B. In some embodiments, a particular anti-reflux valve 42 may be disposed distal to the junction of a side port fluid pathway with the pathway 24, as illustrated, for example, in FIG. 9C.

Figure 9E:
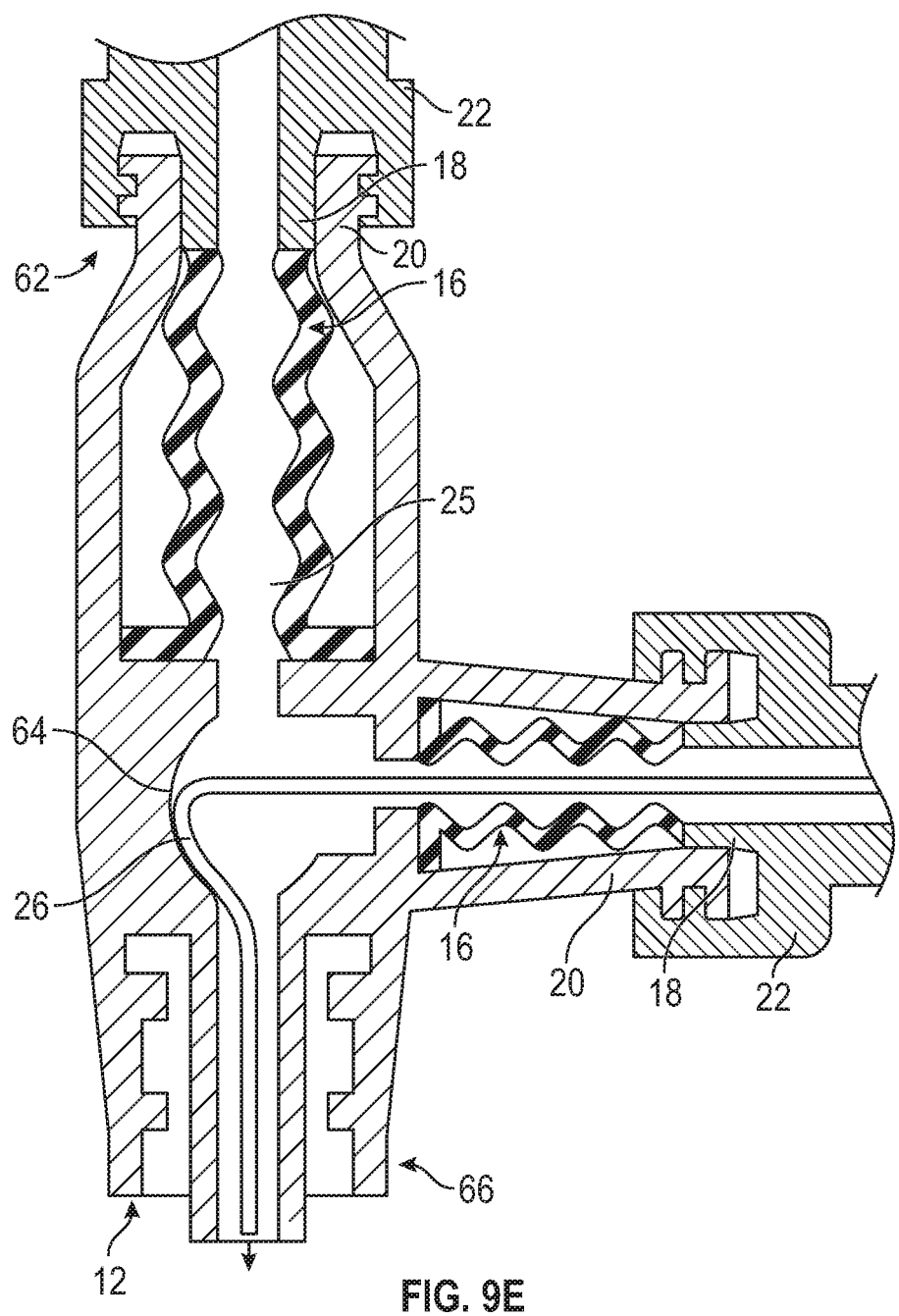
FIG. 9E is a cross-sectional view of the NAC, illustrating an example guide feature, according to some embodiments.

Referring now to FIG. 9E, in some embodiments, the accordion valve 16 may be disposed in a proximal port 62 and/or the side port 54. Additionally, in some embodiments, the post 14 may be disposed in a proximal port 62 and/or the side port 54. In some embodiments, the instrument delivery device 22 may be coupled to the proximal port 62, such as illustrated, for example, in FIG. 2B. In other embodiments, the instrument delivery device 22 may be coupled to the side port 54, as illustrated, for example, in FIG. 9E. In some embodiments, a first instrument 26 may be advanced through the proximal port 62 at a same time as a second instrument 26 is advanced through the side port 54. In these embodiments, an inner surface of the NAC 10 may include a guide feature 64, which may include a tapered or curved surface configured to guide the instrument 26 distally towards a distal port 66.

Figure 9F:
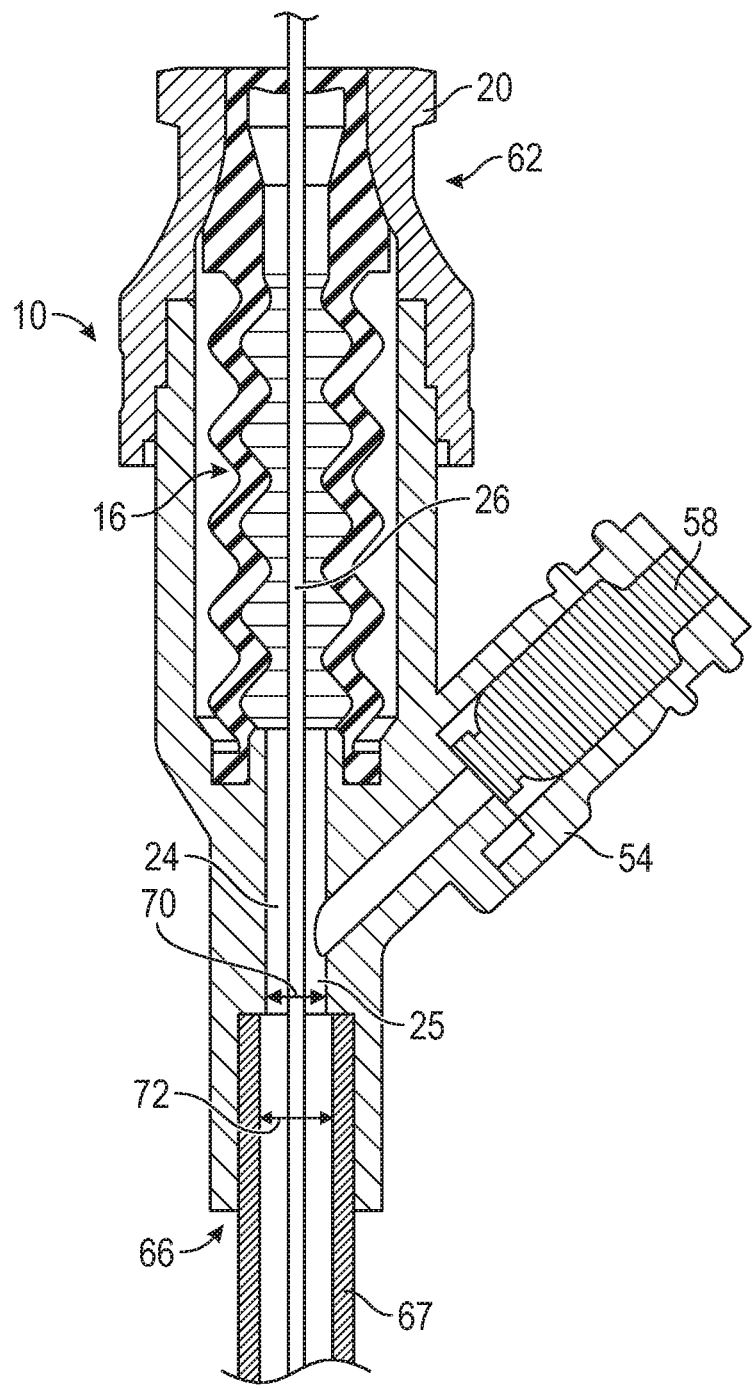
FIG. 9F is a cross-sectional view of the NAC, illustrating an example extension tube, according to some embodiments.

Referring now to FIG. 9F, in some embodiments, the distal end 12 may include an extension tube 67. In some embodiments, a proximal end of the extension tube 67 may be integrated with the distal port 66 and may extend from the distal port 66. In some embodiments, the proximal end of the extension tube 67 may be secured within the distal port 66 via a bond pocket. In some embodiments, a distal end of the extension tube 67 may be coupled to the vascular access device. In some embodiments, the instrument delivery device 22 may be coupled to the proximal port 62, and the instrument may be advanced distally through the NAC 10. In some embodiments, a diameter 70 of the pathway 24 proximate and proximal to the proximal end of the extension tube 67 may be less than or equal to an inner diameter 72 of the extension tube 67 so that the instrument 26 does not catch as the instrument moves distally into the extension tube 67.

Figure 9G:
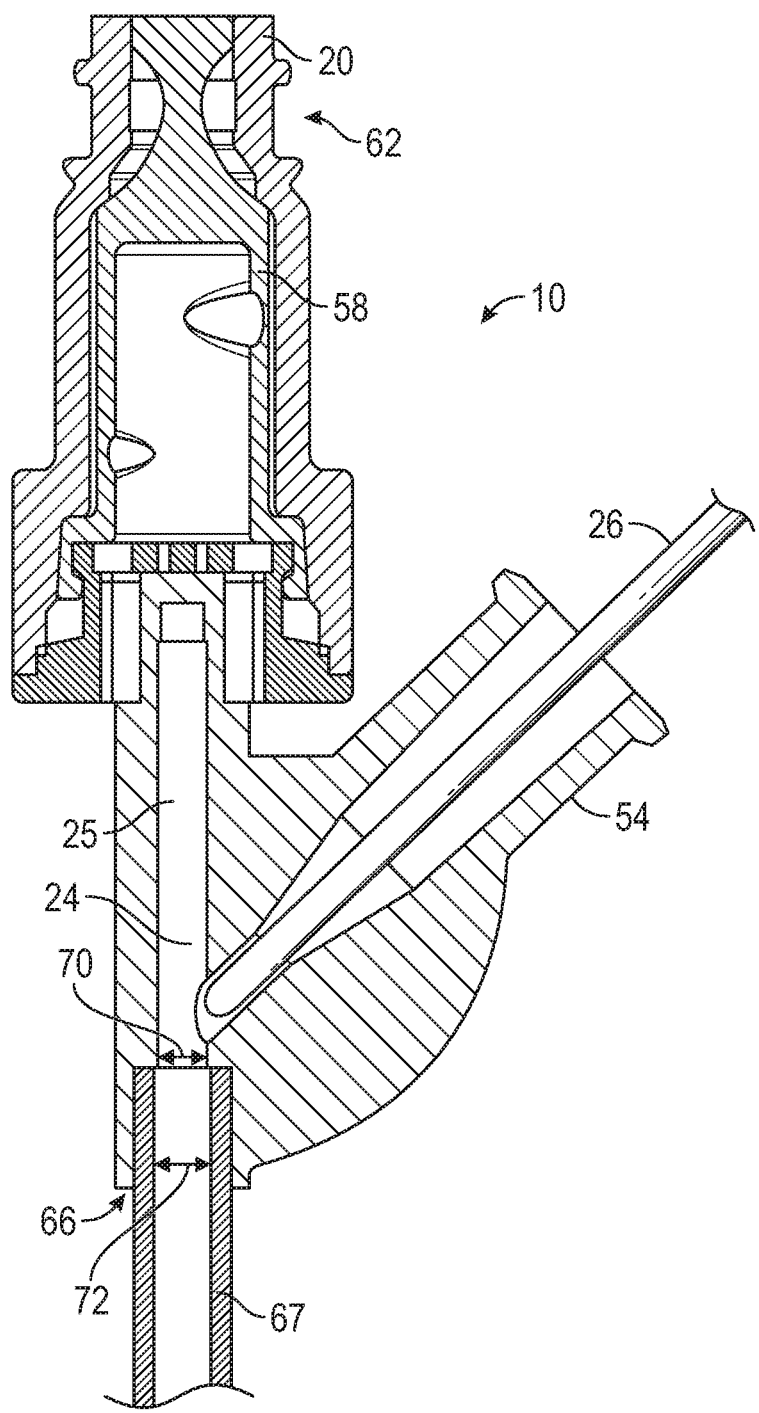
FIG. 9G is a cross-sectional view of the NAC, illustrating the side port having an example luer fitting, according to some embodiments.
Figure 9H:
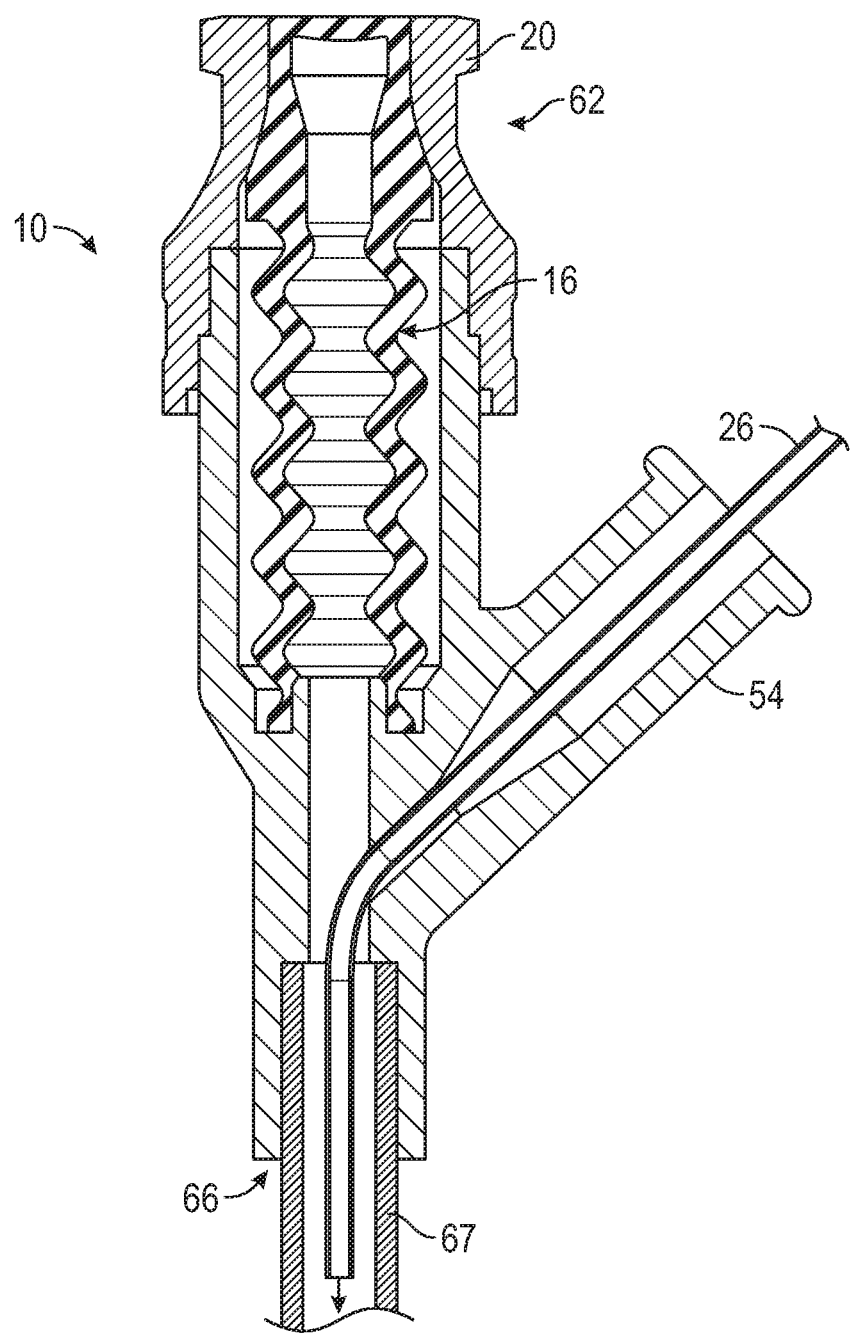
FIG. 9H is a cross-sectional view of the NAC, illustrating the side port having the luer fitting and an example instrument extending therethrough, according to some embodiments.

Referring now to FIG. 9G, in some embodiments, the side port 54 may include a luer fitting, such as, for example, such as, for example, a slip or thread male or female luer fitting. Additionally or alternatively, in some embodiments, the proximal port 62 may include a luer fitting, such as, for example, such as, for example, a slip or thread male or female luer fitting. In some embodiments, the proximal port 62 and/or the side port 54 may include the accordion valve 16 and/or the post 14. In some embodiments, the diameter 70 of the pathway 24 proximate and proximal to the proximal end of the extension tube 67 may be less than or equal to the inner diameter 72 of the extension tube 67 so that the instrument 26 does not catch as the instrument moves distally into the extension tube 67.

In some embodiments, the proximal port 62 and/or the side port 54 may include the PND valve 58, which may be compressible and/or solid without an opening extending therethrough. In some embodiments, the PND valve 58 may not include a fluid pathway through the PND valve 58. In some embodiments, fluid may flow around the PND valve 58 in response to coupling of the medical device 60 to the side port 54, as illustrated, for example, in FIG. 9C. In some embodiments, when the PND valve 58 is not compressed, at least an outer or proximal portion of the PND valve 58 may extend across an entirety of a diameter of the side port 54, which may block the side port 54. In some embodiments, a particular instrument 26 may be inserted distally through the side port 54, as illustrated, for example, in FIG. 9H. Additionally or alternatively, a particular instrument 26 may be inserted distally through the proximal port 62.

It should be understood that the embodiments may be combined. In further detail, a feature illustrated in or described with respect to any particular Figure of the present disclosure may be combined a feature or features of one or more other Figures of the present disclosure. For example, the accordion valve 16 illustrated in FIGS. 2A-2B may include or correspond to the accordion valve 16 of FIGS. 1A-1B, according to some embodiments.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A needleless access connector, comprising:
   a body, comprising:
      a proximal end configured to couple to an instrument delivery device; and
      a distal end configured to couple to a peripheral intravenous catheter assembly;
   an accordion valve disposed within the body between the proximal end and the distal end, wherein the accordion valve comprises an accordion portion, wherein in response to compression of the accordion portion and opening of the accordion valve, a straight pathway extending through the proximal end and the distal end is exposed such that an instrument of the instrument delivery device may move distally from the proximal end to the distal end through the straight pathway without bending; and
   a post configured to extend through the accordion valve when the accordion valve is open, wherein a proximal end of the post is flexible.

2. The needleless access connector of claim 1, wherein the accordion valve comprises a rigid portion, wherein the rigid portion is disposed proximal to the accordion portion.

3. The needleless access connector of claim 1, wherein the accordion valve comprises a rigid portion disposed on an inner surface of the accordion valve, wherein the rigid portion contacts the post.

4. The needleless access connector of claim 1, wherein a proximal end of the accordion valve comprises a rigid portion.

5. The needleless access connector of claim 1, further comprising a male luer fitting configured to slide between a proximal position and a distal position, wherein in response to the male luer fitting sliding from the proximal position to the distal position, the male luer fitting contacts a proximal end of the accordion valve and moves the accordion valve distally.

6. The needleless access connector of claim 5, wherein the accordion valve comprises a slit, the slit opens in response to contact from the male luer fitting and prior to the accordion valve contacting the post.

7. The needleless access connector of claim 1, further comprising an anti-reflux valve disposed within the body between the proximal end and the distal end.

8. The needleless access connector of claim 7, further comprising another anti-reflux valve disposed within the body between the proximal end and the distal end.

9. The needleless access connector of claim 7, wherein the body comprises a first piece that comprises the anti-reflux valve and a second piece that comprises the accordion valve, wherein a luer fitting of the first piece is coupled to a corresponding luer fitting of the second piece.

10. The needleless access connector of claim 9, wherein the second piece comprises a side port and an extension tube extending from the side port.

11. The needleless access connector of claim 1, wherein the distal end is coupled to the peripheral intravenous catheter assembly.

12. The needleless access connector of claim 1, further comprising a side port, wherein the side port comprises another valve, wherein the other valve is compressible such that fluid flows around an outer surface of the other valve to pass the other valve.

13. The needleless access connector of claim 1, wherein the distal end comprises an extension tube, wherein the extension tube extends outwardly from a distal port.

14. A needleless access connector, comprising:
a body, comprising:
a proximal end configured to couple to an instrument delivery device, the proximal end comprising a proximal opening;
a distal end configured to couple to a peripheral intravenous catheter assembly, the distal end comprising a distal opening; and
a lumen extending between the proximal end and the distal end; and
an accordion valve disposed within the body between the proximal end and the distal end, wherein the accordion valve comprises an accordion portion, wherein in response to compression of the accordion portion and opening of the accordion valve, a straight pathway extending through the proximal end and the distal end is exposed such that an instrument of the instrument delivery device may move distally from the proximal end to the distal end through the straight pathway without bending;
an anti-reflux valve disposed within the body between the proximal end and the distal end; and
another anti-reflux valve disposed within the body between the proximal end and the distal end, wherein the lumen is closed between the distal opening of the distal end of the body and the proximal opening of the proximal end of the body.

15. The needleless access connector of claim 14, wherein the anti-reflux valve is adjacent to the another anti-reflux valve.

16. A needleless access connector, comprising:
a body, comprising:
a proximal end configured to couple to an instrument delivery device; and
a distal end configured to couple to a peripheral intravenous catheter assembly;
an accordion valve disposed within the body between the proximal end and the distal end, wherein the accordion valve comprises an accordion portion, wherein in response to compression of the accordion portion and opening of the accordion valve, a straight pathway extending through the proximal end and the distal end is exposed such that an instrument of the instrument delivery device may move distally from the proximal end to the distal end through the straight pathway without bending; and
an anti-reflux valve disposed within the body between the proximal end and the distal end,
wherein the body comprises a first piece that comprises the anti-reflux valve and a second piece that comprises the accordion valve, wherein a luer fitting of the first piece is coupled to a corresponding luer fitting of the second piece, wherein the second piece comprises a side port and an extension tube extending from the side port.

* * * * *